United States Patent [19]
Kropfgans et al.

[11] Patent Number: 6,150,551
[45] Date of Patent: Nov. 21, 2000

[54] PROCESS FOR PREPARING LOW-CHLORIDE OR CHLORIDE-FREE ALKOXYSILANES

[75] Inventors: Frank Kropfgans; Hartwig Rauleder, both of Rheinfelden, Germany

[73] Assignee: Degussa Huels Aktiengesellschaft, Frankfurt, Germany

[21] Appl. No.: 09/432,802

[22] Filed: Nov. 3, 1999

[30] Foreign Application Priority Data

Nov. 6, 1998 [DE] Germany .......................... 198 51 147
Aug. 31, 1999 [DE] Germany .......................... 199 41 283

[51] Int. Cl.$^7$ ................................. C07F 7/08; C07F 7/18
[52] U.S. Cl. .......................... 556/471; 556/466; 556/445; 556/446
[58] Field of Search ..................................... 556/466, 471, 556/445, 446

[56] References Cited

U.S. PATENT DOCUMENTS

| | | | |
|---|---|---|---|
| 4,697,027 | 9/1987 | Sugihara et al. ......................... | 556/466 |
| 4,732,996 | 3/1988 | Moorhead et al. ...................... | 556/466 |
| 4,774,347 | 9/1988 | Marko et al. ............................ | 556/466 |
| 4,827,008 | 5/1989 | Gousetis et al. ......................... | 556/466 |
| 5,084,588 | 1/1992 | Ocheltree et al. ....................... | 556/466 |
| 5,104,999 | 4/1992 | Satoh ....................................... | 556/466 |
| 5,210,254 | 5/1993 | Ritscher et al. ......................... | 556/466 |
| 5,247,117 | 9/1993 | Yamazaki et al. ....................... | 556/466 |
| 5,260,470 | 11/1993 | Goebel et al. .......................... | 556/466 |
| 5,616,755 | 4/1997 | Seiler et al. . | |
| 5,698,726 | 12/1997 | Rauleder et al. . | |
| 5,914,421 | 6/1999 | Bank et al. .............................. | 556/466 |

*Primary Examiner*—Paul F. Shaver
*Attorney, Agent, or Firm*—Oblon, Spivak, McClelland, Maier & Neustadt, P.C.

[57] ABSTRACT

A process for preparing an alkoxysilane with an acidic chloride content of less than 10 ppm by weight, comprising:

reacting a chlorosilane with an alcohol in a water-free and solvent-free phase to form a product mixture containing alkoxysilane and residual acidic chloride, with removal of resultant hydrogen chloride from the product mixture, then adding liquid or gaseous ammonia, in an amount corresponding to a stoichiometric excess, based on the content of acidic chloride, to form an ammonia-containing product mixture, treating the ammonia-containing product mixture at a temperature between 10 and 50° C., wherein the ammonia and acidic chloride undergo neutralization, to form a crude product, and optionally, then separating off a salt formed in the course of neutralization, from the crude product, and recovering the alkoxysilane by distilling the crude product.

20 Claims, No Drawings

PROCESS FOR PREPARING LOW-CHLORIDE OR CHLORIDE-FREE ALKOXYSILANES

BACKGROUND OF THE INVENTION

1. Field of the Invention

The present invention relates to a process for preparing alkoxysilanes which are low in acidic chloride or essentially free from acidic chloride.

2. Discussion of the Background

It is known that alkoxysilanes can be prepared by reacting the corresponding chlorosilanes with an alcohol in accordance, for example, with DE 28 00 017 C2 or EP 0 107 765 P2.

A concern in the course of such procedures is generally to maximize esterification and obtain a good product yield. The survival of unreacted fractions of chlorosilane and hydrogen chloride in the form of what are known as hydrolyzable or acidic chlorine compounds—acidic chloride for short—in the product is not wanted. Within the group of organoalkoxysilanes, it is generally only the aminoalkylalkoxysilanes that include not only acidic chloride but also residues of nonhydrolyzable chlorine compounds, such as chloroalkylalkoxysilane, since such compounds are starting compounds in the preparation of the aminoalkylalkoxysilanes; cf. EP 0 741 137 A1. For the present invention, aminoalkylalkoxysilanes are excluded from the group of alkoxysilanes.

In the light of present-day applications of alkoxysilanes, such as, for example, as adhesion promoters, for hydrophobicization in building protection products, for crosslinking plastics, for modifying surfaces, in glass fiber sizes, for example, and as starting materials for further reaction stages, to name but a few applications, it is therefore necessary to provide products having a very low content of acidic chloride.

In the text below any reference to a chloride-free alkoxysilane is to a product whose acidic chloride content is less than 10 ppm by weight—i.e., which is essentially free from acidic chloride. The detection limit for determining acidic chloride in alkoxysilanes is currently <1 ppm by weight (as determined by argentometric titration in anhydrous acidic solution with potentiometric endpoint determination—AN-SAA-0411).

EP 0 223 210 A2 discloses a method of purifying alkoxysilanes comprising hydrolyzable and nonhydrolyzable chlorine compounds, in which the alkoxysilane is heated in the presence of acid clay or a heavy metal halide, then brought into contact with a neutralizing agent, such as metallic sodium, metallic calcium, alkali metal hydroxide, sodium carbonate, magnesium oxide, alkali metal alcoholate, ammonia, organic amines, alkylene oxides or ortho esters, and separated from the other components by means, for example, of filtration or distillation. In addition, the filter residues arising from this method must be washed with solvent, in a laborius procedure, to remove all silane before they can be disposed of as special waste, or must be worked up and recycled, in a likewise laborious and costly procedure. The heating of said alkoxysilanes in the presence of acid clay or a heavy metal halide is also laborious and can result in unwanted secondary reactions. It is known, for instance, that when chloroalkylalkoxysilanes are heated in the presence of a metal halide, such as iron chloride, aluminum chloride and copper chloride, to name but a few, they are broken down in a process which is accompanied by the liberation of HCl and the formation of alkenylalkoxysilanes. Product discoloration, the formation of mixed esters, and condensation reactions are also observed. Furthermore, owing to traces of the heavy metal halide that is employed, alkoxysilanes obtained by such a method do not in general meet the stringent requirements of the food industry in respect, for example, of plastic packaging or pipes for drinking-water.

DE-A 25 21 399 reveals a process for preparing arninoalkylsilanes in which a reaction mixture obtained by arninating a chloroalkylalkoxysilane is admixed prior to work up with an amount of metal alcoholate equivalent to the amount of chloroalkylsilane and/or chloride present in the mixture. This preparation process makes use of solvents or diluents, such as toluene, hexane or alcohol.

EP 0 282 846 A2 discloses a process for preparing alkoxysilanes with a low content of chlorine compounds by stepwise esterification of chlorosilanes with alcohols in the liquid phase, with removal of the resulting hydrogen chloride. The alkoxysilanes obtained in this way, which still contain a low level of chlorine compounds, are reacted with metal alcoholate—which based on the proportion of chlorine compounds is added in a stoichiometric excess—at a temperature in the range from 80 to 200° C. in the presence or absence of a solvent, such as toluene or xylene, and the alkoxysilane is separated by filtration, for example, from the salts that have been formed. With this process, the long reaction times at relatively high operating temperatures are not very advantageous.

In addition, EP 0 486 279 B1 discloses a process comparable to the abovementioned processes which is intended to remove acidic impurities from alkoxysilanes and which uses, as a neutralizing agent, the metal salt of a sterically hindered amine or an alkali metal alcoholate of a sterically hindered alcohol at a temperature of up to 80° C. over 1 to 2 hours, the neutralized alkoxysilane being distilled. Neutralizing agents of this kind are not available in sufficient quantities for the industrial scale and the separate additional preparation of the neutralizing agent would be complex, costly and therefore ruled out on economic grounds.

EP 0 532 872 B1 likewise discloses a process for preparing alkoxysilanes that are contaminated with hydrolyzable chlorine atoms, where the alkoxysilanes are reacted with an alcohol in a pressure reactor in the presence or absence of excess amounts of a neutralizing agent, reaction taking place at above the boiling point of the alcohol used and under the autogenous pressure, and the salt produced—if appropriate—is separated off and the excess alcohol is removed from the product by distillation. Neutralizing agents disclosed in this case include ammonia, organic amines and sodium alcoholates. It is known that under the abovementioned conditions chloroalkylalkoxysilanes, in particular, are able to react with ammonia or with organic amines to form aminoalkylalkoxysilanes or, in the presence of alcohols and with alcoholates, to form alkyloxyalkylalkoxysilanes.

EP 0 563 883 B1 discloses a process for neutralizing acidic halides in alkoxysilanes which provides for the alkoxysilane to be brought into contact first with a metal alcoholate as a base, which, based on the content of the acidic halide, is added in a stoichiometric excess, and subsequently with an acidic salt which, based on the proportion of the residual base present in excess in the alkoxysilane, is employed in a stoichiometric excess. Here too, the salts are separated by filtration from the product, which can if desired be purified further by stripping off residual alcohol or by distillation. In addition, EP 0 563 883 B1 refers to problems in terms of the color quality of alkoxysilanes, these problems being observed during the work up, in particular during the neutralization and subsequent work up of the alkoxysilanes.

SUMMARY OF THE INVENTION

It is an object of the present invention to provide a simple and, from an industrial point of view, economical process which enables alkoxysilanes which are low in acidic chloride or essentially free from acidic chloride to be prepared.

It has surprisingly now been found that alkoxysilanes which are to be low in acidic chloride or substantially free from acidic chloride are obtainable with particular simplicity and economy and, in particular, that ammonia is a highly suitable and cost-effective neutralizing agent in the preparation of alkoxysilanes when a chlorosilane and/or an organofunctional chlorosilane is reacted with an alcohol, generally at atmospheric pressure. i.e. preferably at atmospheric pressure ±0.5 bar abs., with particular preference at atmospheric pressure ±0.3 bar abs., in a water- and solvent-free phase and the resultant hydrogen chloride is removed from the product mixture, then liquid or gaseous ammonia is added, with the amount of ammonia employed, based on the content of acidic chloride with respect of the alkoxysilane, corresponding to a stoichiometric excess, the ammonia-containing product mixture is treated at a temperature between 10 and 50° C., preferably between 30 and <40° C., the resultant salt is separated, if desired, from the crude product, and the crude product is aftertreated, if desired, with a base and the alkoxysilane is obtained from the crude product by distillation.

Products prepared in accordance with the invention stand out by virtue of an acidic chlorine content which is preferably <5 ppm by weight and extends down to the region of the analytical detection limit for acidic chloride. Furthermore, the process of the invention provides products notable for their very good color quality and excellent purity. In particular, however, the process of the invention is also noteworthy as an industrial process and because of its particular economy.

The present invention therefore provides a process for preparing alkoxysilanes which are low in acidic chloride or essentially free from acidic chloride, by reacting a chlorosilane with an alcohol in a water-free and solvent-free phase with removal of the resultant hydrogen chloride from the product mixture, then adding liquid or gaseous ammonia, with the amount of ammonia employed, based on the content of acidic chloride, corresponding to a stoichiometric excess, treating the ammonia-containing product mixture at a temperature between 10 and 50° C., and if desired then separating off the salt formed in the course of neutralization from the crude product, and recovering the alkoxysilane by distilling the crude product.

DETAILED DESCRIPTION OF THE INVENTION

The process of the invention is preferably operated batchwise. Alternatively, the present process can be operated as a continuous process. In addition, the present process is suitably operated in the liquid phase under an inert gas, with the inert gas used preferably being nitrogen.

Preferred alkoxysilanes of the process of the invention are of the general formula I or II

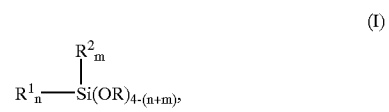

where
  R is a linear or branched alkyl group having 1 to 4 carbon atoms or a glycol ether unit of the formula $-\{(CH_2)_y-O\}_z-R^3$, in which y is 2, 4, 6 or 8, z is 1, 2, 3 or 4 and $R^3$ is a linear or branched alkyl group having 1 to 8 carbon atoms,
  $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms,
  $R^2$ is a linear or branched alkyl group having 1 to 4 carbon atoms, and
  n is 0 or 1 or 2, m is 0 or 1 and (n+m) is 1 or 2 or 3, and

where
  $R^4$ is a linear or branched alkyl group having 1 to 8 carbon atoms or a glycol ether unit of the formula $-\{(CH_2)_y-O\}_z-R^5$ in which y is 2, 4, 6 or 8, z is 1, 2, 3 or 4 and $R^5$ is a linear or branched alkyl group having 1 to 8 carbon atoms.

In the present process the alkoxysilane can be prepared by reacting a chlorosilane, such as 2-chloroethyltrichlorosilane, vinylmethyldichlorosilane, allyltrichlorosilane, 3-allyloxypropyltrichlorosilane, butyltrichlorosilane, pentyltrichlorosilane, cyclopentyltrichlorosilane, cyclopentylmethyldichlorosilane, phenyltrichlorosilane, cyclohexyltrichlorosilane, octylmethyldichlorosilane, dodecyltrichlorosilane, benzyltrichlorosilane, benzylmethyldichlorosilane, 2-phenylethyltrichlorosilane or diphenyldichlorosilane or, with particular preference, tetrachlorosilane, methyltrichlorosilane, dimethyldichlorosilane, trimethylchlorosilane, ethyltrichlorosilane, 3-chloropropyltrichlorosilane, 3-chloropropylmethyldichlorosilane, cyclohexylmethyldichlorosilane, vinyltrichlorosilane, propyltrichlorosilane, propylmethyldichlorosilane, isobutyltrichlorosilane, amyltrichlorosilane, octyltrichlorosilane, hexadecyltrichlorosilane and hexadecylmethyldichlorosilane, with for example a monohydric primary alcohol having 1 to 20 carbon atoms, such as methanol, ethanol, propanol or butanol, or with a monoether of polyalkylene glycols, such as methyl, ethyl, propyl or butyl glycol, or with a di-, tri- or tetramethylene glycol monomethyl, monoethyl, monopropyl or monobutyl ether, or with a dihydric aliphatic alcohol, such as ethylene glycol, 1,2-propylene glycol or 1,2-butylene glycol, or with a diol having 3 to 12 carbon atoms, where the carbon chain can be straight or branched, to name but a few alcohols, with liberation of hydrogen chloride.

In general, the reaction of the chlorosilane with the alcohol takes place under reflux conditions. In some cases, as with haloorganoalkoxysilanes, for example, esterification is more difficult. In the case of the present process it is usual to conduct esterification at a temperature in the range from 30 to 200° C. under atmospheric pressure ±0.5 bar abs. The reaction is suitably conducted at a lower temperature, preferably at a temperature in the range between 40 and 120° C., with particular preference from 50 to 90° C. and, with very particular preference, from 60 to 80° C.

In order to remove the hydrogen chloride resulting from the reaction of chlorosilane and alcohol it is preferred in the process of the invention to add alcohol in liquid form continuously and at the same time an unreacted fraction of the alcohol employed is drawn off from the top as a gas phase, so that the alcohol employed serves additionally as an HCl stripper. In this case it is also possible to operate under reduced pressure. By means of this comparatively simple but, in the case of the present process, highly effective procedure of HCl stripping it is possible with the process of the invention to achieve virtually complete esterification and so, advantageously, to raise the conversion rates to levels of up to 99.9%.

The alcohol employed in the process of the invention is, in particular, methanol, ethanol, n-propanol, isopropanol, methylglycol, ethylglycol or a mixture of two or more of the abovementioned alcohols.

With particular preference, the alkoxysilanes set out below are prepared by the process of the invention:

tetramethoxysilane, tetraethoxysilane, tetrapropoxysilane, methylglycol orthosilicate, ethylglycol orthosilicate, methyltrimethoxysilane, methyltriethoxysilane, dimethyldimethoxysilane, dimethyldiethoxysilane, ethyltrimethoxysilane, ethyltriethoxysilane, 2-chloroethyltriethoxysilane, vinyltrimethoxysilane, vinyltriethoxysilane, vinylmethyldiethoxysilane, vinyltris(2-methyloxyethoxy)silane, phenyltrimethoxysilane, 2-phenylethyltrimethoxysilane, diphenyldimethoxysilane, propyltrimethoxysilane, propyltriethoxysilane, 3-chloropropyltrimethoxysilane, 3-chloropropyltriethoxysilane, propylmethyldimethoxysilane, propylmethyldiethoxysilane, 3-chloropropylmethyldimethoxysilane, 3-chloropropylmethyldiethoxysilane, isobutyltrimethoxysilane, isobutyltriethoxysilane, amyltrimethoxysilane, amyltriethoxysilane, octyltrimethoxysilane, octyltriethoxysilane, cyclohexyltrimethoxysilane, cyclohexylmethyldimethoxysilane, hexadecyltrimethoxysilane, hexadecyltriethoxysilane.

In the case of a process of the invention which is carried out batchwise the product mixture can, after esterification, be initially neutralized. For this purpose the product mixture following the esterification is cooled preferably to a temperature between 10 and 50° C. and ammonia is added with thorough mixing, with the ammonia suitably being employed in a stoichiometric excess based on the content of acidic chloride in the product mixture with respect to the alkoxysilane. Ammonia which is not consumed can be stripped off from the product mixture under reduced pressure and the resultant ammonium salt can be separated off by means, for example, of pressure filtration. Initial neutralization is suitably conducted when more than 1% by weight of acidic chloride, based on the alkoxysilane, is present in the product mixture following esterification. The use of ammonia as a neutralizing agent is also particularly advantageous because ammonia is a comparatively mild base and nucleophile.

It has additionally been found that if the acidic chloride in alkoxysilanes is neutralized at a relatively high temperature or during the actual esterification of the chlorosilane there is a possibility of secondary reactions occurring which markedly restrict the product yield.

In the process of the invention, therefore, before beginning the recovery of the low-chloride or substantially chloride-free alkoxysilane, the ammonia is added and the product mixture from the esterification, which generally contains less than 1% by weight of acidic chloride, is treated, the addition of ammonia to the product mixture suitably being conducted at a temperature in the range between 10 and 50° C. In particular, the bringing together of the product mixture and ammonia and the subsequent treatment of the product mixture, take place with thorough mixing—for example, with stirring. In this case ammonia is preferably employed in a stoichiometric excess, with particular preference of an up to 5-fold molar excess, based on the content of acidic chloride in the product mixture. The ammonia is suitably introduced via a dip pipe whose outlet is preferably located below the liquid level of the product mixture in the reaction chamber.

In the process of the invention, the ammonia-containing product mixture is preferably treated at a pressure in the range from atmospheric pressure to 1.5 bar abs. In the process of the invention, the ammonia-containing product mixture is suitably treated for from 10 minutes to 8 hours. In addition, said product mixture is treated preferably at a temperature between 10 and 40° C., with particular preference between 30 and <40° C. Subsequently, the ammonia-containing product mixture can be devolatilized under reduced pressure. Alternatively, devolatilization can take place in a distillation stage.

To recover the low-chloride or substantially chloride-free alkoxysilane from the product mixture thus treated, however, it is also possible first to filter the ammonium chloride-containing crude product and then to distill the filtrate. Preferably, in the course of filtration the crude product has a temperature of 5 to 30° C., in particular from 10 to 20° C. An alternative in the process of the invention for recovering the low-chloride or substantially chloride-free alkoxysilane is to work up the ammonia- and/or ammonium chloride-containing crude product by distillation.

The distillation is suitably conducted under reduced pressure, in the course of which the liquid-phase temperature can be adapted to the requirements of the respective alkoxysilane and the pure product is suitably taken off from the top of the colurn. If desired, however, the pure product can also be obtained by means of a flash distillation or thin-film distillation.

A particular advantage, furthermore, especially with respect to the economy of the process of the invention, is that, preferably, the ammonium chloride is discharged essentially with the distillate residue of the distillation and it is possible to omit an additional step of filtration.

It has also been found that in some of the product mixtures neutralized in said manner, i.e., in the crude product, and also in a few of the distilled products, it was still possible to detect traces of acidic chloride.

In an effort to achieve as low as possible a residual content of acidic chloride in the pure product—in particular, down to the limit of detectability of acidic chloride in alkoxysilanes—it is particularly advantageous, furthermore, if the crude product produced in the process of the invention is aftertreated with a base prior to its distillative work up. For this purpose said crude product is preferably transferred to the still of the distillation column, then first of all the residual amount of acidic chloride still present in the crude product is determined, an amount of alkali metal alcoholate or alkaline earth metal alcoholate equivalent to this is added to the crude product, the resultant mixture is aftertreated with thorough mixing at a temperature in the range from 10 to 40°

C. and then the crude product thus aftertreated is worked up by distillation to obtain the alkoxysilane. With particular preference, the aftertreatment of the crude product is conducted at from 30 to <40° C. for from 10 to <60 minutes, with very particular preference at from 32 to 38° C. for from 15 to 45 minutes. In the process of the invention, sodium methanolate or sodium ethanolate, suitably present in an alcoholic solution corresponding to the alcoholate, is employed for the aftertreatment of the crude product. The distillation of the crude product thus aftertreated could also be carried out without harm with respect to the color number and clarity of the end product, in the presence of the neutralization products obtained by the aftertreatment of the crude product. Alkoxysilanes prepared in this way then generally have, advantageously, an acidic chloride content of less than 10 ppm by weight, preferably <5 ppm by weight and, with particular preference, of down to the detection limit.

Products obtained in accordance with the process of the invention generally feature high product purity (according to analysis by gas chromatography: >99%), an acidic chloride content of <10 ppm by weight—down to the detection limit, excellent stability on storage. optimized and reproducible hydrolysis behavior, and particularly economic preparation costs. The products obtainable in accordance with the invention are, in an outstanding and advantageous way, water-clear products having an APHA color number of <5, and for this reason, and also as a consequence of an extremely minimal level of impurities, possess a broad spectrum of possible applications.

Having generally described this invention, a further understanding can be obtained by reference to certain specific examples which are provided herein for purposes of illustration only and are not intended to be limiting unless otherwise specified.

EXAMPLE 1

Comparative Example A

Preparation of 3-chloropropyltrimethoxysilane (CPTMO) according to EP 0 282 846 A2

212 kg (1 kmol) of 3-chloropropyltrichlorosilane (CPTCS) are charged at 50 to 60° C. to a batch esterification reactor and a total of 110 kg (3.4 kmol) of methanol are metered in over the course of 5 hours. The methanol is added by means of a dip pipe below the liquid level. When the addition of methanol is complete, the crude product is held at reflux at about 80° C. for 2 hours more. The HCl formed in the course of the reaction is driven off from the reaction mixture by means of a dry $N_2$ stream. Subsequently, the crude ester formed is diluted with about 200 kg of toluene, neutralized at 80° C. with sodium methoxide solution (about 20 mol % excess, based on 1 mol of hydrolyzable chlorine in the product) and cooled to room temperature. Sodium chloride formed is filtered off and the filtrate is worked up by (vacuum) distillation.

Removal of the low boilers (methanol, toluene) gives about 161 kg (81%) of CPTMO with a gas-chromatographic purity of about 94% by weight CPTMO and about 6% by weight 3-methoxypropyltrimethoxysilane (MOPTMO) and a hydrolyzable chloride content of about 25 ppm. The distillation residue formed (about 40 kg, consisting of siloxanes and oligomers) is discarded.

Comparative Example B

Preparation of CPTMO according to EP 0 532 872 B1

The crude CPTMO product, prepared in accordance with Example 1, Comparative Example A and diluted with toluene but not neutralized (hydrolyzable chloride content about 4.8% by weight) is treated at about 80° C. for one hour in accordance with the indications in EP 0 532 872 B1 in a pressure autoclave with methanol and ammonia (about 10 mol % excess, based on the hydrolyzable chloride content). The crude product is cooled, freed from precipitated ammonium chloride by pressure filtration (Seitz filter) (residual hydrolyzable chloride content about 85 ppm) and purified by fractional distillation in vacuo. This distillation gives about 85% by weight CPTMO having a gas-chromatographic purity >98% by weight, a MOPTMO content <0.5% by weight and a hydrolyzable chloride fraction of 46 ppm.

Example C

Preparation of CPTMO 212 kg (1 kmol) of 3-chloropropyltrichlorosilane (CPTCS) are charged at 50 to 60° C. to a batch esterification reactor and are reacted with a total of 110 kg (3.4 kmol) of methanol over the course of 5 hours. The methanol is metered in using a dip pipe below the liquid level. In the course of the addition of methanol, the internal reactor temperature is chosen by continuous reheating such that the crude ester mixture is maintained continually at reflux but the internal temperature does not exceed 110 to 115° C. To remove the HCl formed, the whole of the reaction is conducted under a slight subatmospheric pressure (about 100 mbar) with simultaneous distillative removal of unreacted methanol (HCl-stripping alcohol). However, the stripping process is begun only after about 60% of the stoichiometric amount of methanol has been consumed. In addition, a further 40 kg of methanol is metered in to the boiling reaction mixture, for stripping, but is immediately distilled off again from the reactor, together with the HCl formed, and is employed again in the next reaction batch.

After the end of metered addition of methanol, the acidic mixture is cooled to room temperature and the hydrolyzable chloride content is determined by titration with 0.1 N NaOH (residual chloride content about 0.5 to 1.0 ml of 0.1 N NaOH). Neutralization is carried out conventionally directly in the synthesis reactor by introducing gaseous ammonia below the liquid surface (dip pipe) with continuous stirring and cooling of the reaction mixture to about 30 to 40° C.

The end of neutralization is indicated by the consumption of about 5 ml of 0.1 N HCl during the titration. After further cooling of the crude product to about 10 to 20° C., the precipitated ammonium chloride is separated off by pressure filtration and the filter cake is washed if desired with a little methanol and dried with gaseous nitrogen.

The joint filtrates are transferred to the distillation still and the residual hydrolyzable chloride content is determined by means of argentometric titration. Depending on the desired end-product quality, the crude product can be distilled directly, or still-dissolved hydrolyzable chloride can be converted to sodium chloride by stoichiometric addition of sodium methoxide solution (30 to 40° C., 30 minutes of additional neutralization with stirring).

After the end of the neutralization, the crude product is freed from excess ammonia by means of fractional distillation in vacuo, and is purified, and remaining salt is discharged together with the distillation residue (without further filtration).

This gives about 95% by weight of CPTMO having a GC purity >99%, a MOPTMO content <0.1% and a hydrolyzable chloride content <10 ppm ($NH_3$ is used as neutralizing agent).

When ammonia gas is used and the product is subsequently aftertreated with sodium methoxide solution, about 95% by weight of CPTMO is obtained having a GC purity of 99%, a MOPTMO content <0.3% and a hydrolyzable chloride content <5 ppm.

EXAMPLE 2

Comparative Example A

Preparation of vinyltriethoxysilane (VTEO) according to EP 0 282 846 A2

In accordance with the procedure described in Exanple 1, Comparative Example A, 161.5 kg (1 kmol) of vinyltrichlorosilane (VTC) are reacted with a total of 152 kg (3.3 kmol) of ethanol and the product is neutralized with sodium methoxide solution (21% strength in ethanol) in 20 mol % excess (based on 1 mol of hydrolyzable chloride in the crude product) and worked up by distillation following filtration.

This gives about 127 kg (86%) of VTEO having a GC purity of 97.5%, a tetraethoxysilane content of 2500 ppm, a hydrolyzable chloride content of 17 ppm and a color number of 10 APHA.

Comparative Example B

Preparation of VTEO according to EP 0 532 872 B1

In accordance with the procedure described in Example 1, Comparative Example B, VTEO crude product prepared as in Example A but not neutralized (hydrolyzable chloride content about 2.1% by weight) is treated in a pressure autoclave with ethanol and ammonia (about 10 mol % excess of $NH_3$, based on hydrolyzable chloride content) at 100° C. for one hour. Filtration and distillation give about 88.5% by weight of VTEO having a GC purity of 97.8%, a tetramethoxysilane content of <800 ppm, a hydrolyzable chloride content of 64 ppm and a color number of 5 APHA.

Example C

Preparation of VTEO

In accordance with the procedure described in Example 1, Example C, 161.5 kg (1.0 kmol) of VTC are reacted with a total of 152 kg (3.3 kmol) of ethanol using the stripping process, and the reaction mixture is cooled to room temperature and neutralized with gaseous ammonia under continual cooling. The end of neutralization is indicated by the consumption of about 5 ml of 0.1 N HCl in the titration.

Following the removal of the precipitated ammonium chloride by pressure filtration (as in Example 1, Example C), the crude product is freed from excess ammonia by fractional distillation, and is purified, and remaining salt is discharged together with the distillation residue. Distillative purification gives about 91% by weight of VTEO having a purity >99%, a tetraethoxysilane content <500 ppm, a color number <5 APHA and a hydrolyzable chloride content <10 ppm (use of ammonia). In the case of the combined use of ammonia and subsequent aftertreatment with sodium ethoxide solution in the distillation still, the hydrolyzable chloride content can be reduced to <1 ppm with no change in yield or GC purity.

Example D

Continuous preparation of VTEO

In a continuous esterification plant consisting of reactor column and light ends column, about 100 kg/h of vinyltrichlorosilane and from 80 to 90 kg/h of ethanol are metered simultaneously into the reactor column at about 60° C. under atmospheric pressure, where they are reacted. Hydrogen chloride formed is taken off from the top of the column, and the strongly acidic silane ester crude product (acidity about 5000 ppm) leaves the reactor column in the bottom section and is metered by means of a conveying pump into a second esterification column (light ends column). In the light ends column, the not yet fully reacted chlorosilane fraction (about 5000 ppm) is after-esterified by addition of a small amount of further ethanol (from about 10 to 20 kg), and HCl which is still dissolved in the crude product is driven off at the top of the light ends column at the boiling point of the crude product (about 80 to 90° C.) and metered back into the reactor column. The desorbed crude product leaves the light ends column at the bottom and, after cooling by means of a plurality of heat exchangers, is pumped off into a crude-product tank. The crude ester prepared in this way features a high GC purity and low residual acidity (acidity not more than 200 ppm, VTEO content >98%, siloxane content <1%, ethanol content <1%).

The crude VTEO product is neutralized with gaseous ammonia in analogy to Example C, filtered and purified—if desired after treatment with sodium ethoxide solution—by means of fractional vacuum distillation (continuous or batch distillation). Using ammonia gives about 93% by weight of VTEO having a GC purity >99%, a tetraethoxysilane content <500 ppm, a color number <5 APHA and a hydrolyzable chloride content <10 ppm.

When ammonia and sodium ethoxide solution are used, the hydrolyzable chloride content can be reduced to <1 ppm with no change in yield or GC purity.

EXAMPLE 3

Comparative Example A

Preparation of hexadecyltrimethoxysilane according to EP 0 282 846 A2

In accordance with the procedure described in Example 1, Comparative Example A, 360 kg (1 kmol) of hexadecyltrichlorosilane are reacted with a total of 110 kg (3.4 kmol) of methanol and the product is neutralized with sodium methoxide solution (30% strength in methanol) in 20 mol % excess (based on 1 mol of hydrolyzable chloride in the crude product) and is worked up by distillation after filtration. This gives about 280 kg (81%) of hexadecyltrimethoxysilane having a GC purity of 98.5% (isomer mixture), a color number of 10 APHA and a hydrolyzable chloride content of 12 ppm.

Comparative Example B

Preparation of hexadecyltrimethoxysilane according to EP 0 532 872 B1

In accordance with the procedure described in Example 1, Comparative Example B, crude product prepared in accordance with Example 3, Comparative Example A, but not neutralized (hydrolyzable chloride content about 1.8% by weight) is treated in a pressure autoclave with methanol and ammonia (about 10 mol % excess of $NH_3$, based on the hydrolyzable chloride content) at about 100° C. for one hour. Filtration and distillation give about 86% of hexadecyltrimethoxy-silane having a GC purity of 98.4% (isomer mixture), a color number of <10 APHA and a hydrolyzable chloride content of 47 ppm.

Example C

Preparation of hexadecyltrimethoxysilane

In accordance with the procedure described in Example 1, Example C, 360 kg (1 kmol) of hexadecyltrichlorosilane are reacted with a total of 100 kg (3.1 kmol) of methanol over a metering time of 12 hours and the product is neutralized with gaseous ammonia at room temperature. The neutralization endpoint is reached at from 5 to 7 ml of 0.1 N HCl (titration). After removal of the ammonium chloride formed, the crude ester is purified by fractional distillation in vacuo.

Use of ammonia alone gives about 94% by weight of hexadecyltrimethoxysilane having a GC purity >99%

(isomer mixture), a color number <5 APHA and a hydrolyzable chloride content of 9 ppm.

When ammonia and sodium methoxide solution are used simultaneously, the hydrolyzable chloride content can be reduced to <1 ppm with virtually no change in yield or GC purity.

EXAMPLE 4

Comparative Example A
Preparation of tetra(2-methoxyethoxy)silane (CM) according to EP 0 282 846 A2

In accordance with the procedure described in Example 1, Comparative Example A, 170 kg (1 kmol) of tetrachlorosilane are reacted with a total of 335 kg (4 kmol) of methyl glycol and the product is neutralized with sodium methoxide solution (30% strength in methanol) in 20 mol % excess (based on 1 mol of hydrolyzable chloride in the crude product) and worked up by filtration with subsequent distillation.

This gives about 284 kg (86.5%) of tetra(2-methoxyethoxy)silane having a GC purity of 97.3%, a 2-chloroethoxytris(2-methoxyethoxy)silane content of 1.9%, a color number of 15 APHA and a hydrolyzable chloride content of 27 ppm.

Comparative Example B
Preparation of tetra(2-methoxyethoxy)silane according to EP 0 532 872 B1

In accordance with the procedure described in Example 1, Comparative Example B, crude product prepared in accordance with Example 4, Comparative Example A, but not neutralized (hydrolyzable chloride content about 2.1% by weight) is treated in a pressure autoclave with methyl glycol and ammonia (about 10 mol % excess of $NH_3$, based on the hydrolyzable chloride content) at about 80° C. for one hour. Filtration and distillation give about 88% by weight of tetra(2-methoxyethoxy)silane having a GC purity of 97.8%, a 2-chloroethoxytris(2-methoxyethoxy)silane content of 0.85%, a color number of 10 APHA and a hydrolyzable chloride content of 61 ppm.

Example C
Preparation of tetra(2-methoxyethoxy)silane

In accordance with the procedure described in Example 1, Example C, 170 kg (1 kmol) of tetra-chlorosilane are reacted with a total of 335 kg (4.4 kmol) of methyl glycol using the stripping process and the product is neutralized with gaseous ammonia at room temperature (neutralization endpoint at about 4 ml of 0.1 N HCl). Following separation of the ammonium chloride formed (pressure filtration), the crude ester is purified by fractional vacuum distillation. Distillative work up gives about 91% by weight of tetra(2-methoxyethoxy)silane having a GC purity >99%, a color number <5 APHA, 2-chloroethoxytris(2-methoxyethoxy) silane content <0.4% and hydrolyzable chloride content of 10 ppm. The additional use of sodium ethoxide solution prior to the beginning of distillation makes it possible to reduce the hydrolyzable chloride content to <1 ppm with no change in GC purity or yield.

Example D
Continuous preparation of tetra(2-methoxyethoxy)silane

In a continuous esterification plant consisting of light ends column and reactor column, about 60 kg/h of tetrachlorosilane and from 120 to 130 kg/h of methyl glycol are metered simultaneously into the reactor column at about 55° C. under atmospheric pressure, where they are reacted. Hydrogen chloride formed is taken off at the top of the column, the strongly acidic silane ester crude product leaves the reactor column at the bottom and is metered by means of an appropriate conveying pump into a second esterification column (light ends column). In the light ends column the not yet fully reacted chlorosilane fraction (about 500 ppm) is after-esterified by application of a further quantity of methyl glycol (0.20 kg/h) and HCl which is still dissolved in the crude product is driven off at the top of the column at the boiling point of the crude product (130 to 145° C.). Excess methyl glycol is taken off at the top of the light ends column and is metered back into the reactor column.

The desorbed crude product leaves the light ends column at the bottom and, after cooling by means of a plurality of heat exchangers, is pumped off into a crude product tank. The crude ester prepared in this way features a high purity and low residual acidity (acidity not more than 50 ppm, siloxane content <3%, methyl glycol content <5%, CM content >92%).

The crude silane ester product is neutralized in a separate stirred reactor by adding gaseous ammonia (in accordance with Example 1, Example C) at room temperature until an excess of ammonia is obtained in the crude product corresponding to the consumption of from 5 to 10 ml of 0.1 N HCl (titration). Following pressure filtration to remove the ammonium chloride formed, the filtrate is purified by batchwise or continuous vacuum distillation.

This gives a yield of 92% by weight, a color number <5 APHA, a chloroethoxytris(2-methoxyethoxy)silane content <0.1% and a hydrolyzable chloride content 9 ppm.

If stoichiometric amounts of sodium methoxide solution (based on dissolved hydrolyzable chloride content) are additionally added prior to the beginning of the distillation, the hydrolyzable chloride content can be reduced to <1 ppm with no change in yield or GC purity.

The disclosure of the German priority patent applications 198 51 147.7, filed Nov. 6, 1998, and 199 41 283.9, filed Aug. 31, 1999, are hereby incorporated by reference.

What is claimed is:

1. A process for preparing an alkoxysilane with an acidic chloride content of less than 10 ppm by weight, comprising:
    reacting a chlorosilane with an alcohol in a water-free and solvent-free phase to form a product mixture containing alkoxysilane and residual acidic chloride, with removal of resultant hydrogen chloride from the product mixture,
    then adding liquid or gaseous ammonia, in an amount corresponding to a stoichiometric excess, based on the content of acidic chloride, to form an ammonia-containing product mixture,
    treating the ammonia-containing product mixture at a temperature between 10 and 50° C., wherein the ammonia and acidic chloride undergo neutralization, to form a crude product, and optionally, then separating off a salt formed in the course of neutralization, from the crude product, and
    recovering the alkoxysilane by distilling the crude product.

2. The process as claimed in claim 1, wherein said alcohol is added in liquid form continuously in order to remove said hydrogen chloride and unreacted alcohol is taken off as a gas phase.

3. The process as claimed in claim 1, wherein the ammonia is introduced via a dip pipe whose outlet is located below the liquid level of the product mixture.

4. The process as claimed in claim 1, wherein the ammonia is introduced into the product mixture with stirring and the product mixture is subsequently mixed thoroughly for from 10 minutes to 8 hours.

5. The process as claimed in claim 4, wherein the treatment of the product mixture with ammonia is conducted at a pressure in the range from atmospheric pressure to 1.5 bar abs.

6. The process as claimed in claim 1, wherein the crude product is transferred to a still of a distillation column, any residual amount of acidic chloride present in the crude product is determined, an amount of alkali metal alcoholate or alkaline earth metal alcoholate equivalent to this amount is added to the crude product, the resultant mixture is aftertreated with thorough mixing at a temperature in the range from 10 to 40° C. and then the crude product thus aftertreated is worked up by distillation in order to give the alkoxysilane.

7. The process as claimed in claim 6, wherein the crude product is aftertreated with sodium methanolate or sodium ethanolate.

8. The process as claimed in claim 1, which is conducted continuously.

9. The process as claimed in claim 1, wherein the alcohol is methanol, ethanol, n-propanol, isopropanol, methylglycol, ethylglycol, or a mixture of at least two thereof.

10. The process as claimed in claim 1, wherein the alkoxysilane is of the following general formula I or II

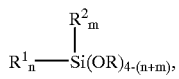
(I)

where

R is a linear or branched alkyl group having 1 to 4 carbon atoms or a glycol ether unit of the formula —{(CH$_2$)$_y$—O}$_z$—R$^3$, in which y is 2, 4, 6 or 8, z is 1, 2, 3 or 4 and R$^3$ is a linear or branched alkyl group having 1 to 8 carbon atoms, R$^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, R$^2$ is a linear or branched alkyl group having 1 to 4 carbon atoms, and n is 0 or 1 or 2, m is 0 or 1 and (n+m) is 1 or 2 or 3, and $$Si(OR^4)_4 \qquad (II),$$

where

R$^4$ is a linear or branched alkyl group having 1 to 8 carbon atoms or a glycol ether unit of the formula —{(CH$_2$)$_y$—O}$_z$—R$^5$ in which y is 2, 4, 6 or 8, z is 1, 2, 3 or 4 and R$^5$ is a linear or branched alkyl group having 1 to 8 carbon atoms.

11. The process as claimed in claim 2, wherein the alkoxysilane is of the following general formula I or II

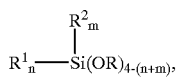
(I)

where

R is a linear or branched alkyl group having 1 to 4 carbon atoms or a glycol ether unit of the formula —{(CH$_2$)$_y$—O}$_z$—R$^3$, in which y is 2, 4, 6 or 8, z is 1, 2, 3 or 4 and R$^3$ is a linear or branched alkyl group having 1 to 8 carbon atoms, R$^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, R$^2$ is a linear or branched alkyl group having 1 to 4 carbon atoms, and n is 0 or 1 or 2, m is 0 or 1 and (n+m) is 1 or 2 or 3, and $$Si(OR^4)_4 \qquad (II),$$

where

R$^4$ is a linear or branched alkyl group having 1 to 8 carbon atoms or a glycol ether unit of the formula —{(CH$_2$)$_y$—O}$_z$—R$^5$ in which y is 2, 4, 6 or 8, z is 1, 2, 3 or 4 and R$^5$ is a linear or branched alkyl group having 1 to 8 carbon atoms.

12. The process as claimed in claim 3, wherein the alkoxysilane is of the following general formula I or II

(I)

where

R is a linear or branched alkyl group having 1 to 4 carbon atoms or a glycol ether unit of the formula —{(CH$_2$)$_y$—O}$_z$—R$^3$, in which y is 2, 4, 6 or 8, z is 1, 2, 3 or 4 and R$^3$ is a linear or branched alkyl group having 1 to 8 carbon atoms, R$^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, R$^2$ is a linear or branched alkyl group having 1 to 4 carbon atoms, and n is 0 or 1 or 2, m is 0 or 1 and (n+m) is 1 or 2 or 3, and $$Si(OR^4)_4 \qquad (II),$$

where

R$^4$ is a linear or branched alkyl group having 1 to 8 carbon atoms or a glycol ether unit of the formula —{(CH$_2$)$_y$—O}$_z$—R$^5$ in which y is 2, 4, 6 or 8, z is 1, 2, 3 or 4 and R$^5$ is a linear or branched alkyl group having 1 to 8 carbon atoms.

13. The process as claimed in claim 4, wherein the alkoxysilane is of the following general formula I or II

(I)

where

R is a linear or branched alkyl group having 1 to 4 carbon atoms or a glycol ether unit of the formula —{(CH$_2$)$_y$—O}$_z$—R$^3$, in which y is 2, 4, 6 or 8, z is 1, 2, 3 or 4 and R$^3$ is a linear or branched alkyl group having 1 to 8 carbon atoms, $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, $R^2$ is a linear or branched alkyl group having 1 to 4 carbon atoms, and n is 0 or 1 or 2, m is 0 or 1 and (n+m) is 1 or 2 or 3, and

  (II), where $R^4$ is a linear or branched alkyl group having 1 to 8 carbon atoms or a glycol ether unit of the formula $—\{(CH_2)_y—O\}_z—R^5$ in which y is 2, 4, 6 or 8, z is 1, 2, 3 or 4 and $R^5$ is a linear or branched alkyl group having 1 to 8 carbon atoms.

14. The process as claimed in claim 5, wherein the alkoxysilane is of the following general formula I or II

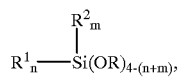  (I)

where

R is a linear or branched alkyl group having 1 to 4 carbon atoms or a glycol ether unit of the formula $—\{(CH_2)_y—O\}_z—R^3$, in which y is 2, 4, 6 or 8, z is 1, 2, 3 or 4 and $R^3$ is a linear or branched alkyl group having 1 to 8 carbon atoms, $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, $R^2$ is a linear or branched alkyl group having 1 to 4 carbon atoms, and n is 0 or 1 or 2, m is 0 or 1 and (n+m) is 1 or 2 or 3, and $Si(OR^4)_4$  (II), where $R^4$ is a linear or branched alkyl group having 1 to 8 carbon atoms or a glycol ether unit of the formula $—\{(CH_2)_y—O\}_z—R^5$ in which y is 2, 4, 6 or 8, z is 1, 2, 3 or 4 and $R^5$ is a linear or branched alkyl group having 1 to 8 carbon atoms.

15. The process as claimed in claim 6, wherein the alkoxysilane is of the following general formula I or II

  (I)

where

R is a linear or branched alkyl group having 1 to 4 carbon atoms or a glycol ether unit of the formula $—\{(CH_2)_y—O\}_z—R^3$, in which y is 2, 4, 6 or 8, z is 1, 2, 3 or 4 and $R^3$ is a linear or branched alkyl group having 1 to 8 carbon atoms, $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, $R^2$ is a linear or branched alkyl group having 1 to 4 carbon atoms, and n is 0 or 1 or 2, m is 0 or 1 and (n+m) is 1 or 2 or 3, and $Si(OR^4)_4$  (II), where $R^4$ is a linear or branched alkyl group having 1 to 8 carbon atoms or a glycol ether unit of the formula $—\{(CH_2)_y—O\}_z—R^5$ in which y is 2, 4, 6 or 8, z is 1, 2, 3 or 4 and $R^5$ is a linear or branched alkyl group having 1 to 8 carbon atoms.

16. The process as claimed in claim 7, wherein the alkoxysilane is of the following general formula I or II

  (I)

where

R is a linear or branched alkyl group having 1 to 4 carbon atoms or a glycol ether unit of the formula $—\{(CH_2)_y—O\}_z—R^3$, in which y is 2, 4, 6 or 8, z is 1, 2, 3 or 4 and $R^3$ is a linear or branched alkyl group having 1 to 8 carbon atoms, $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, $R^2$ is a linear or branched alkyl group having 1 to 4 carbon atoms, and n is 0 or 1 or 2, m is 0 or 1 and (n+m) is 1 or 2 or 3, and $Si(OR^4)_4$  (II), where $R^4$ is a linear or branched alkyl group having 1 to 8 carbon atoms or a glycol ether unit of the formula $—\{(CH_2)_y—O\}_z—R^5$ in which y is 2, 4, 6 or 8, z is 1, 2, 3 or 4 and $R^5$ is a linear or branched alkyl group having 1 to 8 carbon atoms.

17. The process as claimed in claim 8, wherein the alkoxysilane is of the following general formula I or II

  (I)

where

R is a linear or branched alkyl group having 1 to 4 carbon atoms or a glycol ether unit of the formula $—\{(CH_2)_y—O\}_z—R^3$, in which y is 2, 4, 6 or 8, z is 1, 2, 3 or 4 and $R^3$ is a linear or branched alkyl group having 1 to 8 carbon atoms, $R^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, $R^2$ is a linear or branched alkyl group having 1 to 4 carbon atoms, and n is 0 or 1 or 2, m is 0 or 1 and (n+m) is 1 or 2 or 3, and Si(OR$^4$)$_4$ (II), where R$^4$ is a linear or branched alkyl group having 1 to 8 carbon atoms or a glycol ether unit of the formula —{(CH$_2$)$_y$—O}$_z$—R$^5$ in which y is 2, 4, 6 or 8, z is 1, 2, 3 or 4 and R$^5$ is a linear or branched alkyl group having 1 to 8 carbon atoms.

18. The process as claimed in claim 9, wherein the alkoxysilane is of the following general formula I or II $$R^1_n\text{—Si(OR)}_{4-(n+m)}^{R^2_m} \quad (I)$$

where

R is a linear or branched alkyl group having 1 to 4 carbon atoms or a glycol ether unit of the formula —{(CH$_2$)$_y$—O}$_z$—R$^3$, in which y is 2, 4, 6 or 8, z is 1, 2, 3 or 4 and R$^3$ is a linear or branched alkyl group having 1 to 8 carbon atoms, R$^1$ is a linear, branched or cyclic alkyl group having 1 to 20 carbon atoms or a linear, branched or cyclic chloroalkyl group having 1 to 20 carbon atoms or a linear, branched or cyclic alkenyl group having 2 to 10 carbon atoms, R$^2$ is a linear or branched alkyl group having 1 to 4 carbon atoms, and n is 0 or 1 or 2, m is 0 or 1 and (n+m) is 1 or 2 or 3, and Si(OR$^4$)$_4$ (II), where R$^4$ is a linear or branched alkyl group having 1 to 8 carbon atoms or a glycol ether unit of the formula —{(CH$_2$)$_y$—O}$_z$—R$^5$ in which y is 2, 4, 6 or 8, z is 1, 2, 3 or 4 and R$^5$ is a linear or branched alkyl group having 1 to 8 carbon atoms.

19. The process as claimed in claim 1, wherein the alkoxysilane is selected from the group consisting of 3-chloropropyltrimethoxysilane, vinyltriethoxysilane, hexadecyltrimethoxysilane, and tetra(2-methoxyethoxy) silane.

20. The process as claimed in claim 19, wherein the alcohol is methanol, ethanol, n-propanol, isopropanol, methylglycol, ethylglycol, or a mixture of at least two thereof.

* * * * *